(12) United States Patent
Reyneke et al.

(10) Patent No.: US 11,530,172 B2
(45) Date of Patent: Dec. 20, 2022

(54) INTEGRATION OF A STEAM CRACKER WITH ACID ALKYLATION

(71) Applicants: Rian Reyneke, Katy, TX (US); Hendrik Wolterus Klavers, Houston, TX (US)

(72) Inventors: Rian Reyneke, Katy, TX (US); Hendrik Wolterus Klavers, Houston, TX (US)

(73) Assignee: KELLOGG BROWN & ROOT LLC, Houston, TX (US)

( * ) Notice: Subject to any disclaimer, the term of this patent is extended or adjusted under 35 U.S.C. 154(b) by 50 days.

(21) Appl. No.: 16/951,384

(22) Filed: Nov. 18, 2020

(65) Prior Publication Data

US 2022/0153658 A1 May 19, 2022

(51) Int. Cl.
*C07C 2/62* (2006.01)
*C07C 4/04* (2006.01)
(Continued)

(52) U.S. Cl.
CPC ............... *C07C 2/62* (2013.01); *B01D 3/141* (2013.01); *B01D 3/143* (2013.01); *B01J 19/245* (2013.01);
(Continued)

(58) Field of Classification Search
CPC .. C07C 11/08; C07C 2/58; C07C 5/05; C07C 5/48; C07C 7/005; C07C 7/163;
(Continued)

(56) References Cited

U.S. PATENT DOCUMENTS 3,660,520 A * 5/1972 Hemminger ............... C07C 9/16
585/331
9,079,815 B2 7/2015 Mukherjee et al.
(Continued)

FOREIGN PATENT DOCUMENTS

WO 2007135060 A1 11/2007

OTHER PUBLICATIONS

Querini et al., "Deactivation of Solid Acid Catalysts during Isobutane Alkylation with C4 Olefins", Applied Catalysis A General, (1997), pp. 199-215, entire document, especially.
(Continued)

*Primary Examiner* — Sharon Pregler
(74) *Attorney, Agent, or Firm* — Gary M. Machetta

(57) ABSTRACT

Methods and systems for steam cracking a mixed butane containing feed stream are disclosed. The feed stream includes n-butane and isobutane. The disclosed methods and systems entail splitting the feed into an enriched n-butane fraction and an enriched isobutane fraction. The enriched n-butane fraction is provided to the cracking furnaces, which yield the olefin products and also yield C4 species. The C4 species are partially hydrogenated and provided as a reactant feed to an alkylation reaction. The enriched isobutane fraction is also provided to the alkylation reaction, whereby high value alkylate product is produced. The disclosed methods and systems have increase olefins (especially ethylene) yield because the feed to the cracking process is enriched in n-butane. The economics are also improved because high value alkylate product is produced from a portion of the isobutane.

20 Claims, 4 Drawing Sheets

(51) Int. Cl.
 C07C 5/05 (2006.01)
 B01J 19/24 (2006.01)
 B01D 3/14 (2006.01)
 C07C 7/09 (2006.01)

(52) U.S. Cl.
 CPC .................. C07C 4/04 (2013.01); C07C 5/05 (2013.01); C07C 7/09 (2013.01); *B01J 2219/0004* (2013.01)

(58) Field of Classification Search
 CPC .. C07C 9/16; B01J 21/12; B01J 23/892; B01J 23/96; B01J 29/087; B01J 29/7415; B01J 29/7615; B01J 29/7815; B01J 29/90; B01J 35/0006; B01J 37/04
 See application file for complete search history.

(56) References Cited

U.S. PATENT DOCUMENTS

| | | | |
|---|---|---|---|
| 10,179,753 | B2 | 1/2019 | Mukherjee et al. |
| 2013/0204058 | A1 | 8/2013 | Adam et al. |
| 2017/0022126 | A1 | 1/2017 | Mukherjee et al. |
| 2017/0113981 | A1 | 4/2017 | Mukherjee et al. |
| 2017/0247298 | A1 | 8/2017 | Wagner et al. |
| 2019/0218158 | A1 | 7/2019 | Mukherjee et al. |
| 2020/0109096 | A1 | 4/2020 | DiGiulio et al. |

OTHER PUBLICATIONS

Long et al., "Design and Optimization of Heat Integrated Dividing Wall Columns for Improved Debutanizing and Deisobutanizing Fractionation of NGL", Korean Journal of Chemical Engineering, 30(2), pp. 286-294, (2013), entire document, especially p. 286, col. 2, para 3; p. 287, col. 1, para 1-2; p. 289, col. 2, para 1; Figure 1, 6.

Hsu et al., "Gasoline Production", Petroleum Science and Technology, Chapter 10, Jul. 3, 2019 (Jul. 3, 2019), pp. 189-210, entire document, especially p. 190, para 2; p. 191, para 1; Figure 10.1.

Patent Cooperation Treaty; International Search Report and Written Opinion for International Application No. PCT/US21/59024 filed Nov. 11, 2021 dated Mar. 28, 2022 (19 pages).

\* cited by examiner

INTEGRATION OF A STEAM CRACKER WITH ACID ALKYLATION

FIELD OF THE INVENTION

This application relates to steam cracking, and more particularly, to methods and systems for increasing the ethylene yield of a steam cracking process that uses a mixed butane feed, while also yielding an alkylate product.

INTRODUCTION

Steam cracking is a petrochemical process used to convert saturated hydrocarbons into smaller, often unsaturated hydrocarbons. For example, butane is a common feedstock for steam cracking to produce olefins, such as ethylene and propylene. In such a steam cracking operation, the butane feed stock is diluted with steam and heated in a furnace to yield ethylene, propylene, and various other products and byproducts. The butane feed stock encountered in steam cracking operations typically include a mixture of normal butane (n-butane) and iso-butane. For example, a typical butane feed stock may have about 70% n-butane and about 30% iso-butane. Steam cracking of n-butane typically yields about 32-40% ethylene and about 53-57% total olefins. In contrast, steam cracking of iso-butane typically yields about 7-12% ethylene and about 32-35% total olefins. As a result, n-butane is a favored feedstock to produce ethylene, since it has a total olefins yield that is about 20% greater than the yield obtained from iso-butane. Accordingly, there is a need in the art for methods and systems for increasing the olefins yield of mixed butane feedstocks.

SUMMARY

Disclosed herein is a method of producing olefins and alkylate from a feed comprising isobutane and n-butane, the method comprising: fractionating the feed in a first de-isobutanizer column to obtain an enriched n-butane fraction and an enriched isobutane fraction, cracking the enriched n-butane fraction in a cracking furnace to yield the olefins and a C4 product comprising butene, and butadiene, partially hydrogenating the C4 product, and reacting the enriched isobutane fraction and the partially hydrogenated C4 species in an alkylation reaction to yield an alkylation reaction effluent comprising the alkylate. According to some embodiments, the alkylation reaction is a solid acid alkylation reaction. According to some embodiments, the enriched isobutane fraction further comprises propane and wherein the method further comprises: fractionating the enriched isobutane fraction in a depropanizer column to obtain an enriched propane fraction, and providing the enriched propane fraction to the cracking furnace. According to some embodiments, the alkylation reaction effluent further comprises isobutane and wherein the method further comprises: fractionating the alkylation reaction effluent in a second de-isobutanizer column to obtain an enriched alkylate fraction and an enriched isobutane recycle fraction, and recycling the enriched isobutane recycle fraction to the alkylation reaction. According to some embodiments, the enriched alkylate fraction further comprises n-butane and wherein the method further comprises: fractionating the enriched alkylate fraction in a debutanizer column to obtain alkylate product and an enriched n-butane recycle fraction, and recycling the enriched n-butane recycle fraction to the cracking furnace. According to some embodiments, the alkylation reaction effluent further comprises isobutane and wherein the method further comprises: fractionating the alkylation reaction effluent in the first de-isobutanizer column to obtain an enriched alkylate fraction and an enriched isobutane recycle fraction, and recycling the enriched isobutane recycle fraction to the alkylation reaction. According to some embodiments, the enriched isobutane fraction and the enriched isobutane recycle fraction are a combined stream from the first de-isobutanizer column. According to some embodiments, the method further comprises obtaining an enriched propane stream from the first de-isobutanizer column and recycling the enriched propane stream to the cracking furnace. According to some embodiments, the enriched alkylate fraction further comprises n-butane and wherein the method further comprises: fractionating the enriched alkylate fraction in a debutanizer column to obtain alkylate product and an enriched n-butane recycle fraction, and recycling the enriched n-butane recycle fraction to the cracking furnace. According to some embodiments, the first de-isobutanizer column comprises a split column configured so that: the feed is provided to a first side of the first de-isobutanizer column, the alkylation reaction effluent is provided to a second side of the first de-isobutanizer column, and an enriched n-butane stream is removed as a side draw of the first de-isobutanizer column.

Also disclosed herein is a system for producing olefins and alkylate from a feed comprising isobutane and n-butane, the system, comprising: a first de-isobutanizer column configured to fractionate the feed into an enriched n-butane fraction and an enriched isobutane fraction, a cracker configured to crack the enriched n-butane fraction to yield the olefins and a C4 product comprising butene, and butadiene, a partial hydrogenation reactor configured to partially hydrogenate the C4 product, and an alkylation reactor configured to react the enriched isobutane fraction and the partially hydrogenated C4 species to yield an alkylation reaction effluent comprising the alkylate. According to some embodiments, the alkylation reaction is a solid acid alkylation reaction. According to some embodiments, the enriched isobutane fraction further comprises propane and wherein the system further comprises: a depropanizer column configured to fractionate the enriched isobutane fraction to provide an enriched propane fraction, wherein the enriched propane fraction is provided to the cracking furnace. According to some embodiments, the alkylation reaction effluent further comprises isobutane and wherein the system further comprises: a second de-isobutanizer column configured to fractionate the alkylation reaction effluent to provide an enriched alkylate fraction and an enriched isobutane recycle fraction, wherein the enriched isobutane recycle fraction is recycled to the alkylation reaction. According to some embodiments, the enriched alkylate fraction further comprises n-butane and wherein the system further comprises: a debutanizer column configured to fractionate the enriched alkylate fraction to provide alkylate product and an enriched n-butane recycle fraction, wherein the enriched n-butane recycle fraction is recycled to the cracking furnace. According to some embodiments, the alkylation reaction effluent further comprises isobutane, and wherein the first de-isobutanizer column is further configured to fractionate the alkylation reaction effluent to provide an enriched alkylate fraction and an enriched isobutane recycle fraction, wherein the enriched isobutane recycle fraction is recycled to the alkylation reaction. According to some embodiments, the enriched isobutane fraction and the enriched isobutane recycle fraction are a combined stream from the first de-isobutanizer column. According to some embodiments, the first de-isobutanizer column is further configured to provide an enriched propane stream wherein the enriched propane stream is recycled to the cracking furnace. According to some embodiments, the enriched alkylate fraction further comprises n-butane and wherein the system further comprises: a debutanizer column configured to fractionate the enriched alkylate fraction to provide alkylate product and an enriched n-butane recycle fraction, wherein the enriched n-butane recycle fraction is recycled to the cracking furnace. According to some embodiments, the first de-isobutanizer column is a split column configured so that the feed is provided to a first side of the first de-isobutanizer column and the alkylation reaction effluent is provided to a second side of the first de-isobutanizer column.

DETAILED DESCRIPTION

Figure 1:
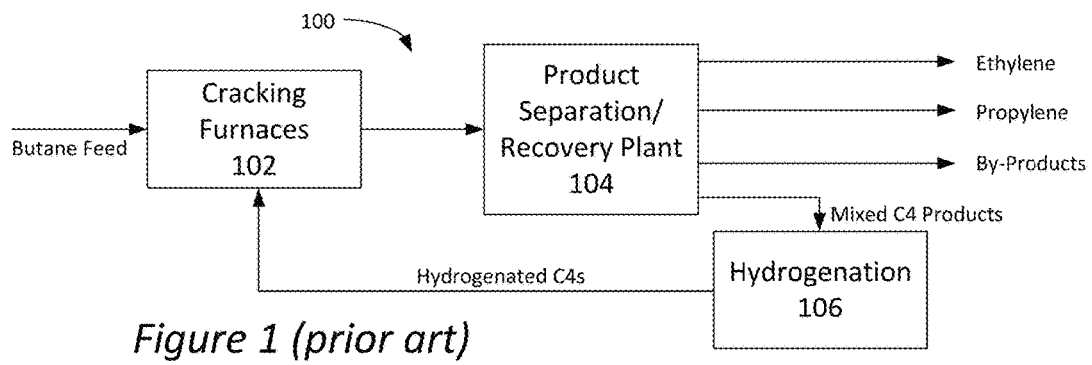
FIG. 1 shows a process for steam cracking a mixed butane stream, in accordance with the prior art.

FIG. 1 is a high-level illustration of a butane steam cracking process 100 as known in the art. In currently used steam cracking processes, butane feed is provided to the steam cracking furnaces 102. As mentioned above, available butane feed streams typically comprise about 70% n-butane and about 30% iso-butane. The butane feed stream is cracked in the cracking furnace and the cracking furnace effluent is provided to a gas separation/recovery plant 104. The gas separation/recovery plant 104 includes various steps for separating the cracking furnace effluent into its constituent components, as is known in the art. For example, the gas separation/recovery plant may include various quench steps, compression, acid gas removal, cold fractionation, etc., for separating the cracking effluent into various streams, such as an $H_2$ rich stream, tail gas, ethylene, propylene, and various other products/by-products. Note that the system may include various recycle loops from the gas separation/recovery plant 104 to the cracking furnaces 102, such as ethane recycle, propane recycle, etc., which are not illustrated. In the illustrated prior art process, one of the streams from the gas separation/recover plant may comprise mixed C4 products, which may be hydrogenated in a hydrogenation step 106 and recycled to the cracking furnaces 102.

As mentioned above, the butane feed stream may contain a significant amount (e.g., about 30%) iso-butane, which is not a preferred cracking feed because cracking of iso-butane has a low yield of olefin. The inventors have discovered that the yield of olefins and the overall economics of a steam cracking process using mixed butanes as a feed stream can be improved by using a process 200, which is illustrated at a high-level in FIG. 2. In the illustrated improved process 200 the mixed butane feed stream is provided to a de-isobutane splitter (DIB) 202, which separates the butane feed into a top iso-butane-rich stream and a bottom n-butane-rich stream. The n-butane rich stream is provided as feed to the cracking furnaces. Since n-butane is the preferred cracking feed, providing an n-butane rich stream to the cracking furnaces increases the relative yield of olefins, specifically ethylene. The iso-butane-rich stream is provided as feed to an alkylation process 204. In the alkylation process 204, the iso-butane from the mixed butane feed is reacted with olefinic C4 species obtained from the cracking process to produce high-value alkylate products.

The improved process 200 differs from the process 100 in several ways. First, the improved process includes a de-isobutane splitter 202 that splits the mixed butane feed into isobutane and n-butane. Ideally, it is desirable to use the de-isobutane splitter to remove as much isobutane as possible from the mixed butane feed so that the feed to the cracking furnace is as enriched as possible in the preferred n-butane feed. However, that consideration must be balanced against the size/energy requirements of the de-isobutane splitter as well as the stoichiometric amount of iso-butane required to match the available olefinic C4s in the alkylation process. According to some embodiments, the de-isobutane splitter removes about 35% of the isobutane from the feed and the remainder of the isobutane goes to the cracking furnaces along with the n-butane. Also, some n-butane is carried along with the isobutane in the overhead stream from the de-isobutane splitter and is thereby provided to the alkylation process 204. As explained in more detail below, the alkylation process may include a further de-isobutane separation process that is configured to further separate isobutane and n-butane from the alkylation reactor effluent. The n-butane separated in that process can be recycled back to the cracking furnaces, further improving the ethylene yield.

Another difference between the improved process 200 and the prior art process 100 is how the unsaturated C4 species generated during the cracking process are treated. In the prior art process, unsaturated C4 species are completely hydrogenated and recycled to the cracking furnaces. In the improved process 200, the unsaturated C4 species generated during the cracking process are partially hydrogenated to provide olefinic C4 species. As explained in more detail below, the olefinic C4 species are an ideal feed to the alkylation process.

Figure 2:
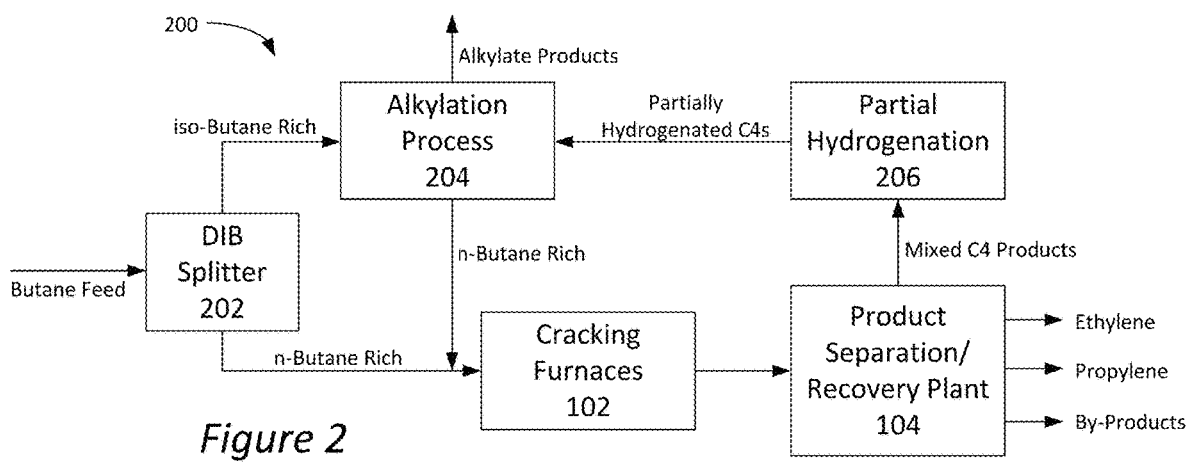
FIG. 2 shows a process for steam cracking a mixed butane stream and making an alkylate product.

The process 200 illustrated in FIG. 2 provides several improvements and benefits over the prior art process 100 (FIG. 1). In the process 200, the DIB 202 splits the mixed butane feed and provides the cracking unit with a feed that is enriched in n-butane. The increase of the preferred n-butane component increases the ethylene yield of the cracker. Less by-product is produced, thereby debottlenecking the process and allowing a higher feed throughput. For example, the inventors have determined that in one embodiment, applying the disclosed process increased the overall mixed butane feed by 27.5% and produced 10% more ethylene (15.7% of the delta feed). The disclosed process also uses the iso-butane of the iso-butane rich stream to produce alkylate, which is a high value product that has emerged as a preferred gasoline blending component. As described in more detail below, solid-acid alkylation, such as KBR's K-SAAT™ alkylation process (KBR Houston, Tex.) meshes synergistically in the disclosed process. The preferred reactant feeds for the alkylation are iso-butane and olefinic C4. With solid-alkylation, such as K-SAAT™ technology it is also possible to supplement the olefinic C4 stream with lighter olefins such as ethylene and propylene to further increase consumption of isobutane and production of alkylate. In the disclosed process, the iso-butane feed is provided from the iso-butane rich stream from the DIB 202 and the olefinic C4 feed is provided by partially hydrogenating the C4 stream from the cracker effluent. The production of high value alkylate product increases the economics of the process. For example, the inventors determined that 84.6% of the delta feed (i.e., 84.6% of the 27.5% greater mixed butane feed realized by applying an embodiment of the disclosed process) was converted to alkylate. So, essentially all of the increased mixed butane feed realized by applying an embodiment of the disclosed process was converted to ethylene and alkylate.

Figure 3:
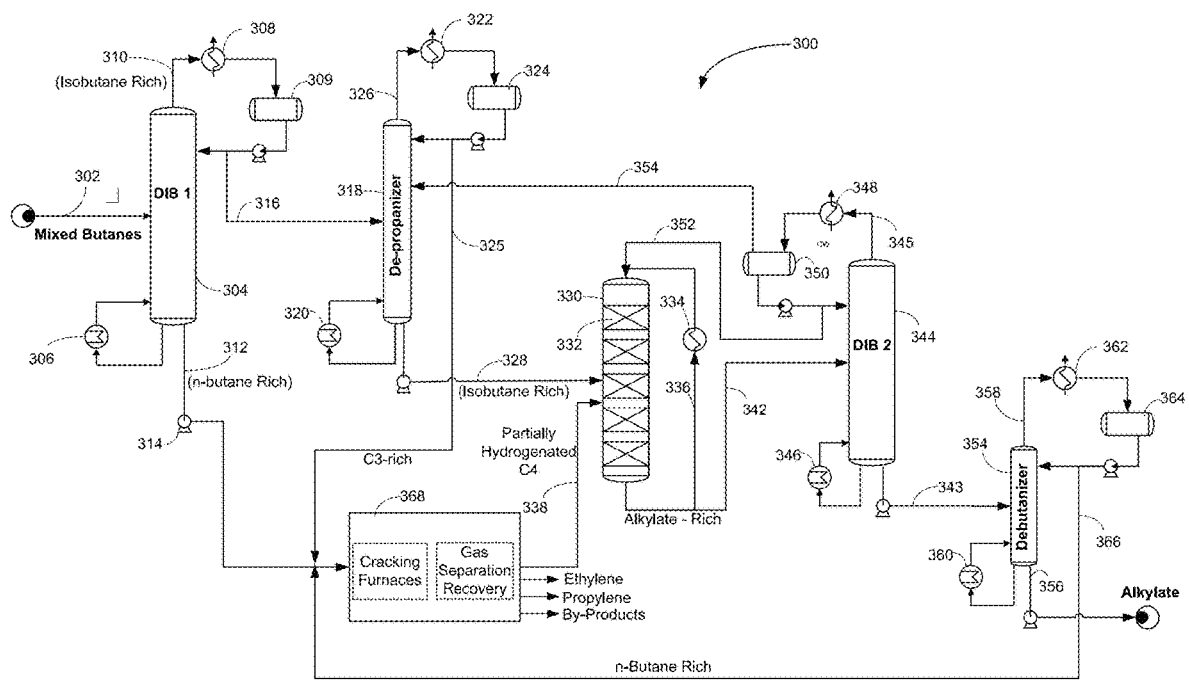
FIG. 3 shows a configuration for steam cracking a mixed butane stream and making an alkylate product.

FIG. 3 illustrates a configuration 300 of an embodiment of the disclosed process 200 (FIG. 2). A mixed butane feed is provided to a first de-isobutane splitter column (DIB 1) 304 via line 302. The de-isobutane splitter column 304 may be a distillation column configured to separate the mixed butane feed into an isobutane rich top stream 310 and an n-butane rich bottom stream 312. The de-isobutane splitter column 304 may be configured with a reboiler 306, a condenser 308, and a reflux drum 309. The reboiler 306 (as well as the reboilers associated with the other columns in the process 300) may be heated using low pressure steam, for example. The condenser 308 (as well as the condensers associated with the other columns in the process 300) may be chilled using cooling water. Pumps, such as pump 314 may be used to facilitate flow throughout the process. Note that additional pumps are illustrated in the illustrated configuration 300 but are not individually labeled with call-out numbers.

According to some embodiments, the mixed butane feed may include some amount of propane, which will be carried with the isobutane rich stream. Accordingly, the isobutane rich stream may be provided to a de-propanizer column 318 via line 316. The de-propanizer column 318 may be equipped with a reboiler 320, a condenser 322 and a reflux drum 324. The de-propanizer column 318 separates C3s (e.g., propane) as a top stream 326, which may be provided to the cracking furnaces via line 325. A propane-depleted isobutane rich stream exits the bottom of the de-propanizer column via line 328 and is provided to an alkylation reactor 330.

According to some embodiments, the alkylation reactor 330 uses solid acid catalyst alkylation technology, for example, a K-SAAT™ (KBR, Houston, Tex.). Aspects of solid acid catalyst alkylation are described in U.S. Pat. Nos. 9,079,815 and 10,179,753, and U.S. Patent Publication No. 2020/0031733, for example, which are hereby incorporated by reference. The alkylation reaction between isobutane and olefins, such as C4 olefins provided by line 338), takes place over a solid acid catalyst on fixed beds 332. The catalyst may be a zeolite catalyst, as described in the referenced patents and may comprise metals, such as platinum, palladium, and/or nickel. Note that while only one reactor 330 is illustrated, some embodiments may include multiple reactors (e.g., 2 or 3 reactors), which allows one or more of the reactors to be regenerated in a staggered cycle while others of the reactors are operating. The reaction is exothermic, and the heat of the reaction can be managed by a heat exchanger 334 located in a recirculation loop 336.

The effluent from the alkylation reactor 330 exiting the reactor via line 342 contains alkylate product, isobutane, as well as other components that may have been carried in the isobutane rich stream, such as n-butane, ethane, and propane. In the illustrated embodiment, alkylation reactor effluent is provided to a second de-isobutanizer column (DIB 2) 344 via line 342. The second de-isobutanizer column 344 separates the alkylation reactor effluent into a bottom stream 343 comprising alkylate product and n-butane and an overhead stream 345 comprising isobutane and lighter components. The second de-isobutanizer column 344 may be equipped with a reboiler 346, a condenser 348 and a reflux drum 350. A stream rich in isobutane is recycled to the alkylation reactor 330 via line 352. The reflux drum 350 may be equipped with a small C3 purge, which may provide C3 materials, such as propane, back to the depropanizer column 318 via line 354.

In the illustrated embodiment, the alkylate rich stream 343 is provided to a debutanizer column 354, which separates the alkylate product as a bottom stream 356 from n-butane, which leaves the debutanizer column as an overhead stream 358. The debutanizer column 354 may be equipped with a reboiler 360, a condenser 362 and a reflux drum 364. The n-butane is recycled to the cracker furnaces via line 366. Note that not all embodiments necessarily require a debutanizer column 354, as illustrated. For example, according to some embodiments, the alkylate product may be obtained as a bottom stream from the de-isobutanizer column 344 and the n-butane rich stream may be obtained as a side-draw from the de-isobutanizer column. However, since the n-butane is being recycled to the cracker, a higher n-butane purity is desirable, and thus, the use of a debutanizer column, as illustrated, may be preferred.

Recall that the mixed butane feed is separated into isobutane rich and n-butane rich streams by the first de-isobutanizer column 304 and that the n-butane rich stream is provided to the cracker furnaces via line 312. In the illustrated process, the cracker furnaces are included in the block 368, which includes the cracker furnaces and various post-cracking equipment of the gas plant (separation/recovery). The cracking furnaces crack the components of the n-butane rich stream and the components are treated and separated to provide the olefinic products (e.g., ethylene, propylene, etc.) and other products and by-products. The cracker effluent comprises various unsaturated C4 species, such as butenes, which may be provided to the alkylation reactor as feed. The cracker effluent may comprise butadiene (e.g., about 15-20% butadiene), which is not a preferred feed to the alkylation reactor. The butadiene may be separated from the effluent, but that process may be unattractive. Another solution is to partially hydrogenate the butadiene in a partial hydrogenator to yield butene (i.e., partially hydrogenated olefinic C4). The partial (selective) hydrogenation of butadiene may be achieved in a liquid phase hydrogenation reactor, typically using a palladium-based catalyst. Typical hydrogenation conditions are in the range of 20-40 barg and 40-100° C. The reaction is exothermic, so a large cooled liquid recycle may be used to maintain the reactor temperature in the target range. The partially hydrogenated olefinic C4 may be provided as feed to the alkylation reactor 330 via line 338

Figure 4:
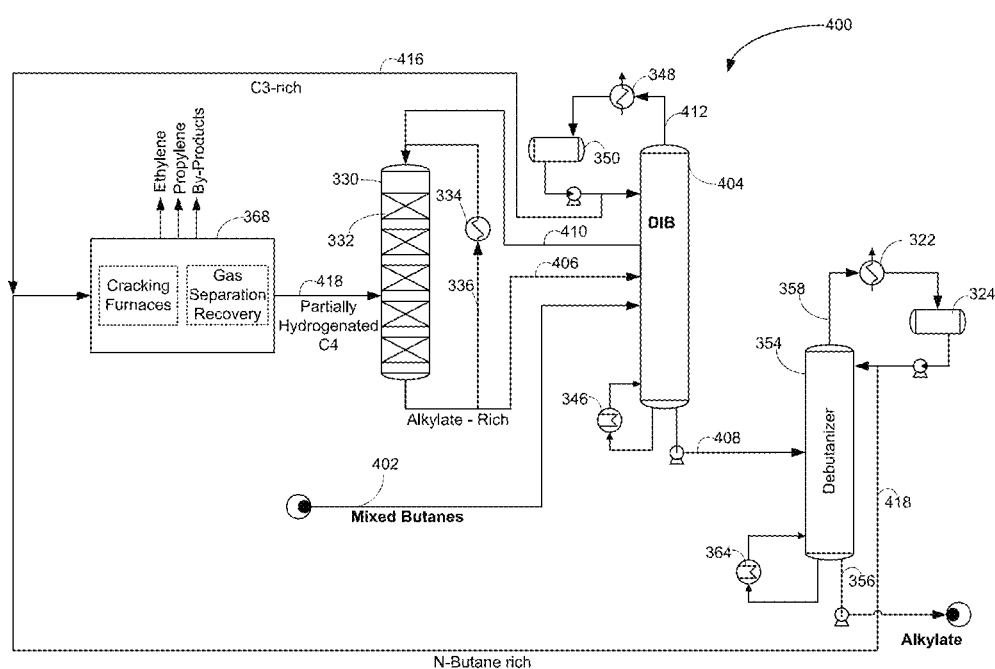
FIG. 4 shows an alternative configuration for steam cracking a mixed butane stream and making an alkylate product, the configuration utilizing a shared de-isobutanizer column.

FIG. 4 illustrates a configuration 400 of an alternative embodiment of the disclosed process 200 (FIG. 2). Note that in the figures, equipment and processes that are common to the various configurations are given like numbers and are not discussed multiple times. In the configuration 400, a common de-isobutanizer column (DIB) 404 is used both to split the mixed butane feed and to handle the effluent of the alkylation reactor. A mixed butane feed is provided to the common de-isobutanizer column 404 via line 402. The alkylate rich reactor effluent is provided to the common de-isobutanizer column 404 via line 406. The common de-isobutanizer column provides a bottom stream 408 comprising mainly alkylate product and n-butane. An isobutane rich stream may be taken as a side draw and recycled to the alkylation reactor via line 410. The overhead stream 412 of the common de-isobutanizer column comprises C3 and some isobutane. The propane-rich overhead stream can be recycled to the cracking furnaces via line 416. As discussed above, the gas separation and recovery section also may include a partial hydrogenation process that provides a partially hydrogenated olefinic C4 feed to the alkylation reactor 330 via line 418. The bottom stream 408 of the common de-isobutanizer column is provided to a debutanizer column, which separates the components into a bottom stream 356 comprising alkylate product and a top stream 358 comprising n-butane. The n-butane may be recycled to the cracking furnaces via line 418.

An advantage of the configuration 400 over the configuration 300 (FIG. 3) is that the configuration 400 has a lower equipment count. However, the configuration 400 may use greater energy. The entirety of the n-butane feed contacts the alkylate product in the common de-isobutanizer column 404. Consequently, the duty of the debutanizer 354 must be greater to re-separate the n-butane from the alkylate, compared to the debutanizer duty required in the configuration 300.

Figure 5:
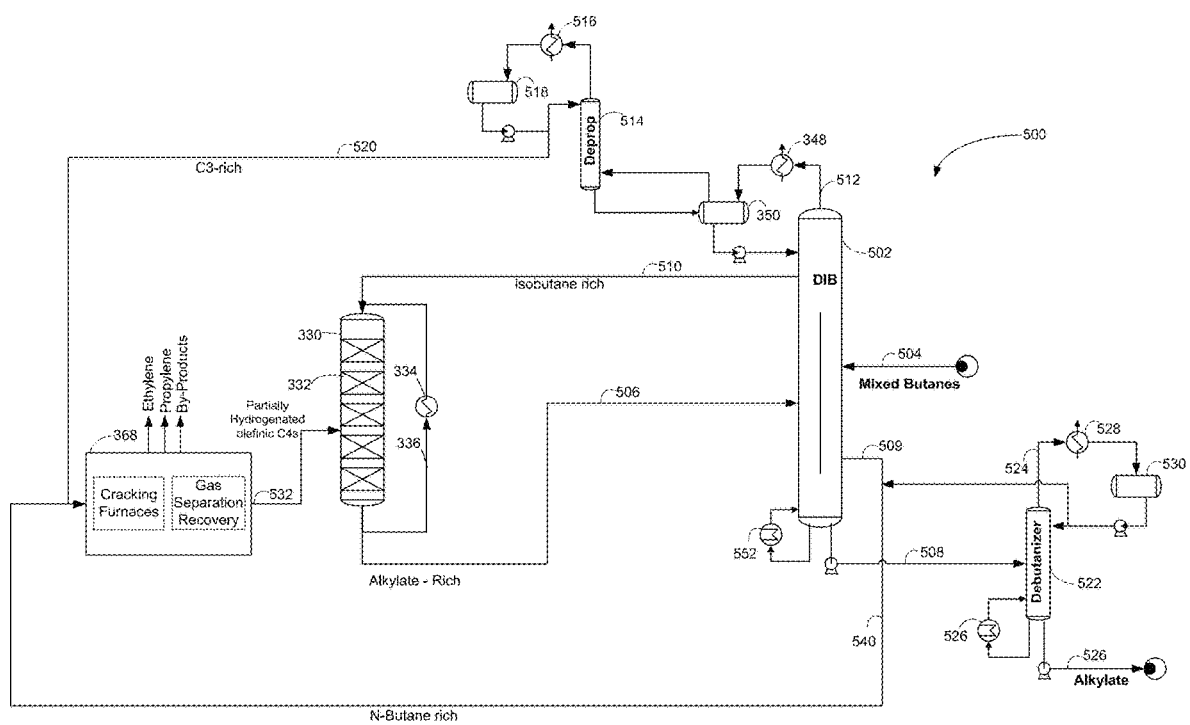
FIG. 5 shows an alternative configuration for steam cracking a mixed butane stream and making an alkylate product, the configuration utilizing a shared split de-isobutanizer column.

FIG. 5 illustrates a configuration 500 of an alternative embodiment of the disclosed process 200 (FIG. 2). The configuration 500 is similar to the configuration 400 (FIG. 4) in the sense that a single de-isobutanizer is used both to split the mixed butane feed and to handle the effluent of the alkylation reactor. However, the de-isobutanizer column of the configuration 500 is a split de-isobutanizer column 502. The mixed butane feed is provided to one side (the right side, in the illustration) of the split de-isobutanizer column 502 via line 504. The alkylate rich reactor effluent is provided to the other side (the left side, in the illustration) of the split de-isobutanizer column 502 via line 506. In this configuration, the entirety of the n-butane feed does not contact the alkylate product effluent. As a result, the 500 configuration is more energy efficient than the configuration 400. The split de-isobutanizer column provides a bottom stream 508 comprising mainly alkylate product and some n-butane. Ideally, most of the n-butane is obtained as a side draw 509 on the feed side (right side in the illustration) of the split de-isobutanizer column and recycled back to the cracking furnaces. An isobutane rich stream may be taken as a side draw from the split de-isobutanizer column and recycled to the alkylation reactor via line 510. The overhead stream 512 of the common de-isobutanizer column comprises C3 and some isobutane. The isobutane content in the overhead stream 512 may be set to allow the use of cooling water for condensing and minimizing tower pressure so that most of the condensing duty (e.g., ~95%) can be done at the warmer temperature (against cooling water) and the remaining condensing duty (e.g. ~5%) is done at the top of the depropanizer column 514 using high-level refrigeration in the condenser 516. The vapor flow within the split de-isobutanizer column 502 can be controlled by the design of the column. The dividing wall may be configured in the center of the column or may be off set in one direction or the other and the height of the dividing wall may also be configured based on the particular implementation (e.g., the relative amounts of feed and reactor effluent). Collection trays may be used to redistribute liquid within the column and external lines may be used to reflux those section separately to meet certain separation targets. The column design will be implementation specific and it is within the ability of a person of skill in the art, based on this disclosure, to design or obtain a suitable split de-isobutanizer column to meet their needs.

The illustrated configuration 500 includes a depropanizer column 514 configured to remove isobutane from the split de-isobutanizer column 502 overhead stream and recycle it back to the split de-isobutanizer column. The depropanizer column 514 may be equipped with a condenser 516 and a reflux drum 518. The C3 components of the de-isobutanizer column overhead stream may be recycled to the cracking furnaces via line 520. The depropanizer column 514 may use a refrigerated condenser to allow a lower de-isobutanizer column pressure and use of low-pressure steam in the de-isobutanizer column reboiler 552.

In the illustrated configuration, the bottom stream 508 from the split de-isobutanizer column 502, which comprises alkylate product and some n-butane, is provided to a debutanizer column 522, which splits the stream into a top stream 524 comprising n-butane and a bottom stream 526 comprising alkylate product. The debutanizer column 522 may be equipped with a reboiler 526, a condenser 528 and a reflux drum 530. A portion of the n-butane top stream 524 can be combined with the side draw stream 509 and recycled to the cracking furnaces as stream 540. As discussed above, the gas separation and recovery section also may include a partial hydrogenation process that provides a partially hydrogenated olefinic C4 feed to the alkylation reactor 330 via line 532.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of producing olefins and alkylate from a feed comprising isobutane and n-butane, the method comprising:
    fractionating the feed in a first de-isobutanizer column to obtain an enriched n-butane fraction and an enriched isobutane fraction,
    cracking the enriched n-butane fraction in a cracking furnace to yield the olefins and a C4 product comprising butene, and butadiene, wherein the olefins are enriched in ethylene,
    partially hydrogenating the C4 product, and
    reacting the enriched isobutane fraction and the partially hydrogenated C4 species in an alkylation reaction to yield an alkylation reaction effluent comprising the alkylate.

2. The method of claim 1, wherein the alkylation reaction is a solid acid alkylation reaction.

3. The method of claim 1, wherein the enriched isobutane fraction further comprises propane and wherein the method further comprises:
    fractionating the enriched isobutane fraction in a depropanizer column to obtain an enriched propane fraction, and
    providing the enriched propane fraction to the cracking furnace.

4. The method of claim 1, wherein the alkylation reaction effluent further comprises isobutane and wherein the method further comprises:
    fractionating the alkylation reaction effluent in a second de-isobutanizer column to obtain an enriched alkylate fraction and an enriched isobutane recycle fraction, and recycling the enriched isobutane recycle fraction to the alkylation reaction.

5. The method of claim 4, wherein the enriched alkylate fraction further comprises n-butane and wherein the method further comprises:
fractionating the enriched alkylate fraction in a debutanizer column to obtain alkylate product and an enriched n-butane recycle fraction, and
recycling the enriched n-butane recycle fraction to the cracking furnace.

6. The method of claim 1, wherein the alkylation reaction effluent further comprises isobutane and wherein the method further comprises:
fractionating the alkylation reaction effluent in the first de-isobutanizer column to obtain an enriched alkylate fraction and an enriched isobutane recycle fraction, and
recycling the enriched isobutane recycle fraction to the alkylation reaction.

7. The method of claim 6, wherein the enriched isobutane fraction and the enriched isobutane recycle fraction are a combined stream from the first de-isobutanizer column.

8. The method of claim 6, further comprising obtaining an enriched propane stream from the first de-isobutanizer column and recycling the enriched propane stream to the cracking furnace.

9. The method of claim 6, wherein the enriched alkylate fraction further comprises n-butane and wherein the method further comprises:
fractionating the enriched alkylate fraction in a debutanizer column to obtain alkylate product and an enriched an enriched n-butane recycle fraction, and
recycling the enriched n-butane recycle fraction to the cracking furnace.

10. The method of claim 6, wherein the first de-isobutanizer column comprises a split column configured so that:
the feed is provided to a first side of the first de-isobutanizer column,
the alkylation reaction effluent is provided to a second side of the first de-isobutanizer column, and
an enriched n-butane stream is removed as a side draw from the first side of the first de-isobutanizer column.

11. A system for producing olefins and alkylate from a feed comprising isobutane and n-butane, the system comprising:
a first de-isobutanizer column configured to fractionate the feed into an enriched n-butane fraction and an enriched isobutane fraction,
a cracker configured to crack the enriched n-butane fraction to yield the olefins and a C4 product comprising butene, and butadiene, wherein the olefins are enriched in ethylene,
a partial hydrogenation reactor configured to partially hydrogenate the C4 product, and
an alkylation reactor configured to react the enriched isobutane fraction and the partially hydrogenated C4 species to yield an alkylation reaction effluent comprising the alkylate.

12. The system of claim 11, wherein the alkylation reaction is a solid acid alkylation reaction.

13. The system of claim 11, wherein the enriched isobutane fraction further comprises propane and wherein the system further comprises:
a depropanizer column configured to fractionate the enriched isobutane fraction to provide an enriched propane fraction, wherein
the enriched propane fraction is provided to the cracking furnace.

14. The system of claim 11, wherein the alkylation reaction effluent further comprises isobutane and wherein the system further comprises:
a second de-isobutanizer column configured to fractionate the alkylation reaction effluent to provide an enriched alkylate fraction and an enriched isobutane recycle fraction, wherein
the enriched isobutane recycle fraction is recycled to the alkylation reaction.

15. The system of claim 14, wherein the enriched alkylate fraction further comprises n-butane and wherein the system further comprises:
a debutanizer column configured to fractionate the enriched alkylate fraction to provide alkylate product and an enriched n-butane recycle fraction, wherein
the enriched n-butane recycle fraction is recycled to the cracking furnace.

16. The system of claim 11, wherein the alkylation reaction effluent further comprises isobutane, and wherein
the first de-isobutanizer column is further configured to fractionate the alkylation reaction effluent to provide an enriched alkylate fraction and an enriched isobutane recycle fraction, wherein
the enriched isobutane recycle fraction is recycled to the alkylation reaction.

17. The system of claim 16, wherein the enriched isobutane fraction and the enriched isobutane recycle fraction are a combined stream from the first de-isobutanizer column.

18. The system of claim 16, wherein the first de-isobutanizer column is further configured to provide an enriched propane stream wherein the enriched propane stream is recycled to the cracking furnace.

19. The system of claim 16, wherein the enriched alkylate fraction further comprises n-butane and wherein the system further comprises:
a debutanizer column configured to fractionate the enriched alkylate fraction to provide alkylate product and an enriched an enriched n-butane recycle fraction, wherein
the enriched n-butane recycle fraction is recycled to the cracking furnace.

20. The system of claim 16, wherein the first de-isobutanizer column is a split column configured so that the feed is provided to a first side of the first de-isobutanizer column and the alkylation reaction effluent is provided to a second side of the first de-isobutanizer column.

* * * * *